United States Patent [19]

Evans et al.

[11] 4,375,703
[45] Mar. 8, 1983

[54] ENDOPROSTHETIC BONE JOINT DEVICES

[75] Inventors: David M. Evans, Farnham Common; Barry O. Weightman, Thames Ditton, both of England

[73] Assignee: National Research Development Corporation, London, England

[21] Appl. No.: 253,513

[22] PCT Filed: Aug. 12, 1980

[86] PCT No.: PCT/GB80/00127
§ 371 Date: Apr. 15, 1981
§ 102(e) Date: Apr. 15, 1981

[87] PCT Pub. No.: WO81/00511
PCT Pub. Date: Mar. 5, 1981

[30] Foreign Application Priority Data

Aug. 17, 1979 [GB] United Kingdom ............... 7928802

[51] Int. Cl.³ ........................... A61F 1/04; A61F 5/04
[52] U.S. Cl. ................................. 3/1.91; 128/92 C
[58] Field of Search ................. 3/1.91, 1.9, 1; 128/92 C

[56] References Cited

U.S. PATENT DOCUMENTS

| | | | |
|---|---|---|---|
| 3,909,853 | 10/1975 | Lennox | 3/1.91 |
| 3,939,496 | 2/1976 | Ling et al. | 3/1.91 |
| 3,990,117 | 11/1976 | Pritchard et al. | 3/1.91 |
| 4,011,603 | 3/1975 | Steffee | 3/1.91 |
| 4,063,314 | 12/1977 | Loda | 3/1.91 |
| 4,131,957 | 1/1979 | Bokros | 3/1.91 |

FOREIGN PATENT DOCUMENTS 939226 2/1956 Fed. Rep. of Germany ......... 3/1.91

Primary Examiner—Richard J. Apley
Assistant Examiner—David J. Isabella
Attorney, Agent, or Firm—Cushman, Darby & Cushman

[57] ABSTRACT

Endoprosthetic metacarpal phalangeal joint devices are well known in various forms including unitary flexible structures for connection between the bones, and others with separate phalangeal and metacarpal components for respective bone connection and inter-engagement or connection for mutual articulation in a hinge action. All such devices are applied individually to respective joints and can tend to fail due to conditions leading to ulnar drift. It is now proposed that this tendency be obviated by mechanically interconnecting a plurality of devices of the latter form in the hand, suitably by use of a common hinge pin. The pin preferably has slight longitudinal curvature to pass through the natural joint centers. The phalangeal components preferably each have a socket for bone connection and a stem for axle connection, the stem being slidably and rotatably received in the socket to accomodate torsional loading.

13 Claims, 2 Drawing Figures

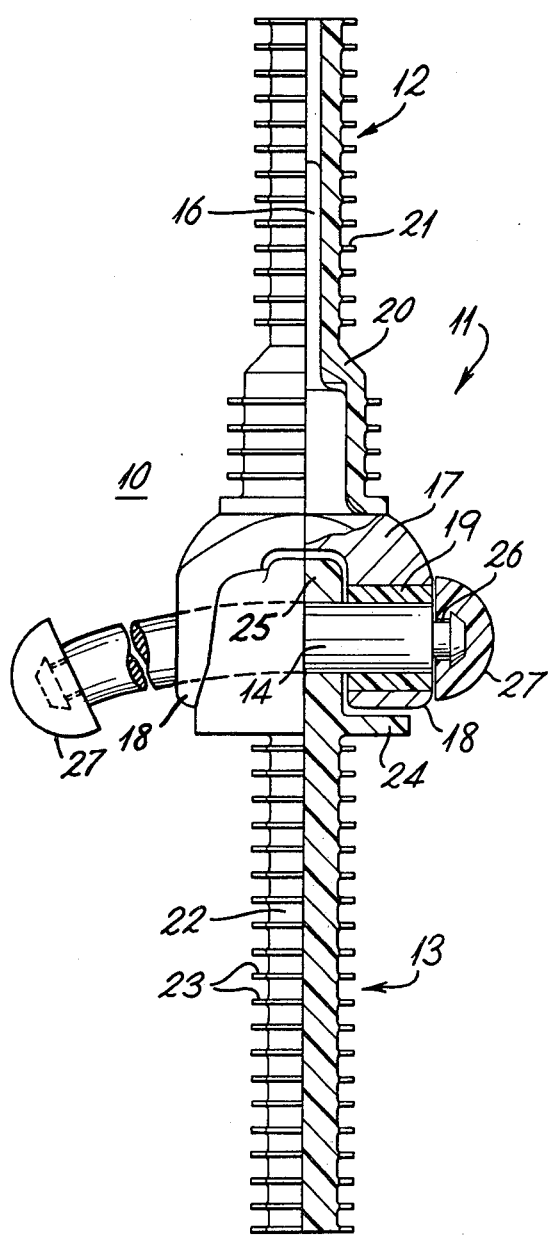
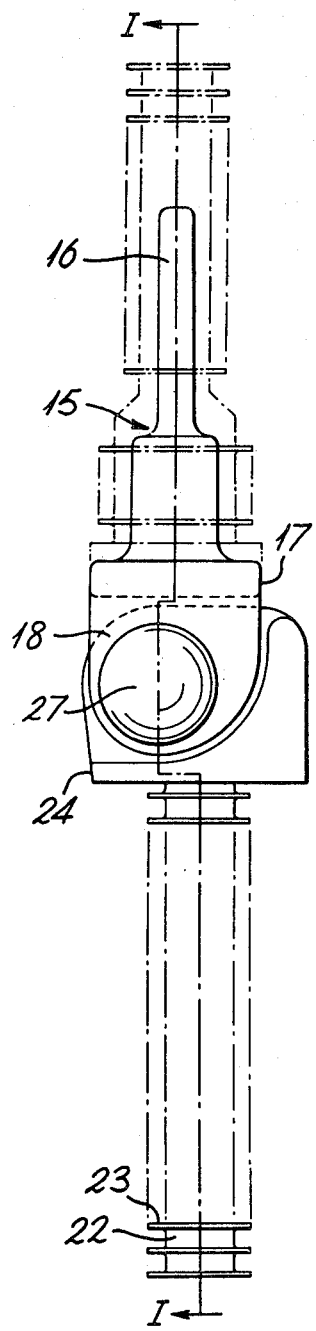
Fig. 1
Fig. 2

ENDOPROSTHETIC BONE JOINT DEVICES

This invention concerns endoprosthetic bone joint devices, and more particularly such devices for the metacarpal phalangeal (hereinafter referred to as MCP) joints.

Endoprosthetic MCP joint devices are already available and are probably best known in a form devised by Swanson involving a one-piece elongate structure of silicone rubber providing terminal portions for respective location in the bones of the joints, and a hinge portion interconnecting the terminal portions. Other forms of MCP devices have been proposed in which separate terminal components are provided and mechanically interlinked by respective mutually articulatory portions. Although the general form of these prior MCP joint devices has been subject to some variety, it is a common feature of all such devices that they are applied individually to joints in a one-to-one manner.

In practice, MCP joint devices are frequently used to combat the results of advanced rheumatoid arthritis and in this event it is common for all of the MCP joints of a hand to be replaced by individual devices. However, this situation is one which is accompanied by so-called ulnar drift in the hand, with the MCP joints becoming subluxated by lateral and dorsal-palmar shear forces, and the consequent movement of the extensor tendons from longitudinal alignment exacerbating the situation.

Moreover, experience indicates that, while the provision of a set of MCP joint devices in such a situation can provide relief for a time, device failure is highly likely and recurring deterioration almost inevitable because the underlying condition remains unchanged and will give rise to stress in the individual devices in a similar manner to that which affected the original joints.

An object of the present invention is to improve this situation and it is proposed in general terms that this be achieved by mechanically interlinking two or more MCP devices in order to effect a mutual stabilisation of the devices and to distribute thereover the deleterious stresses applied to individual ones of the devices.

To this end the present invention provides, in a presently preferred form thereof, an endoprosthetic MCP joint assembly comprising a plurality of devices which each include a pair of components for respective connection to the bones of an individual MCP joint, and which devices include a common hinge pin member for hingedly connecting the components of each of said devices.

Preferably the phalangeal component of each device of the assembly comprises two sub-components of which one is connectable to the bone and the other of which is connectable with the hinge pin member, said other sub-component being slidably and rotatably receivable in said one sub-component.

Also it is preferred that the hinge pin member have slight longitudinal curvature.

It is also preferable that the components should be restrained against dislocation from the pin, and this can be effected by providing stops at the ends of the pin, at least one such stop being separately connectable to the axle, suitably by provision thereof in the form of a snap fit cap. This last feature is appropriate for the presently intended surgical procedure in which the components are first secured to their respective bones and the pin threaded through the components thereafter. Also, it may be appropriate for the two components of each device to be directly connectable, suitably by a snap fit, to facilitate threading of the pin therethrough.

In order that the above and other features of the invention may be more clearly understood, the invention will now be described by way of example with reference to the accompanying drawings, in which:

FIG. 1 is a half-sectional side view, taken on I—I in FIG. 2, of one embodiment of a device according to the invention, and FIG. 2 is an end view of said embodiment.

The assembly of the illustrated embodiment is denoted as a whole by reference numeral 10 and comprises a plurality of similar MCP joint devices 11 of which only one is shown for the sake of simplicity. Each device includes a phalangeal component 12 and a metacarpal component 13, such components being hingedly inter-connected by a single hinge pin member 14 common to all of the devices 11.

Each phalangeal component 12 is in several parts of which one, 15, is metal and comprises a stem 16 having circular cross-sectional shape and joined at one end with the base of a bifurcated enlargement 17. The arms 18 of this enlargement are of like form and are coaxially bored, the common axis of these bores extending perpendicularly to, but slightly off-set from the axis of the stem 16. Also, it is to be noted that the stem 16 is reduced in diameter in a stepped manner towards its free end to afford a strong junction with the enlargement but small transverse dimensions at its end.

Further parts of the component 12 comprise two like bushes 19 of plastic material respectively located in the bores of the arms.

The remaining part of the component 12 is also of plastics material and is a stem socket 20 having an elongate overall form generally similar to that of the stem 16 and having an axial bore complementary with the stem 16. In its more detailed exterior form the socket 20 has longitudinally spaced therealong a plurality of annular fins 21, each fin having a plurality of radial slits spaced circumferentially therearound.

Each metacarpal component 13 is of one-piece plastics material formation and comprises a stem 22 having a plurality of slit fins 23 therealong similar to those of the socket 20. This stem 22 is connected at one end, by way of a diametrally enlarged collar portion 24, to a transversely bored annular arm portion 25 extending longitudinally relative to the stem in a diametral plane thereof. This last portion is related in shape and size to the annular arm portions 18 of the component 12 such that portion 24 can be received between the portions 18 with their respective bores coaxially aligned, and these portions can each receive the pin member 14 therethrough. It is to be noted that the collar 24 extends from its diametral plane relative to the stem 22 along one side of the arm 25. It is also to be noted that the bore of the arm 25 is off-set from the axis of the stem 22, this off-set being directed away from the collar extension and being larger than the similar off-set in the phalangeal component.

The pin member 14 is a substantially circular cylindrical rod of metal having a slight longitudinal curvature and a respective circumferential groove 26 adjacent each end to receive an associated domed end cap 27 of plastics material in a snap fit. Each end cap is of greater diameter than the axle member to serve as a stop at the end thereof.

In use of the illustrated assembly, appropriate MCP joints of the relevant hand are exposed and the bones suitably prepared to receive the metacarpal and phalangeal components, the metacarpal bones preferably being resected during this preparation so that their ends are located on a transverse line corresponding to the longitudinal axis of the axle member. The components are then connected with their respective bones. For this purpose the phalangeal component socket 20 and the metacarpal component stem 22 are pushed into bores of such diameter that the fins 21 and 23 distort by flexure to provide interference fits. The metacarpal component is to be so fitted that the extended part of its collar 24 is located dorsally. The remainder of the phalangeal component is then located by sliding and rotatable receipt of the stem 16 in the bore of socket 20. The bored arms 18 and 25 of the components are then brought into coaxial relationship as mentioned above, it being ensured at this stage that the off-set of the former is in a palmar direction, and the pin member 14 is then threaded successively through the components, whereafter the end caps 27 are connected to the pin member and the joints suitably closed.

As indicated earlier, a benefit of the illustrated assembly in use is that the common pin member distributes the deleterious stresses which can otherwise lead to ulnar drift. Further benefits arise from this and other features of the assembly. The multipart form of the phalangeal component allows rotation between its stem and socket in response to torsional loading which may otherwise cause loosening movement at the socket/bone interface. The pin member linkage of the devices serves a related function in distributing stresses due to axial torque which may otherwise cause loosening at the metacarpal component/bone interface. The off-set locations of the stem axes relative to the pin member axis and the differential nature of these off-sets closely reflects the geometry of the natural joint. The slight curvature of the axle member allows this member to pass through the centres of the natural joints.

During development of the present invention up to the stage of the latest embodiment thereof, namely that just described, some variations in thinking have arisen. One such variation centres on the fact that originally it was contemplated that all four MCP joints in a hand might be treated by one assembly involving a single common pin. However the present thinking is that use of a pair of assemblies each involving two devices and a common pin will be preferable.

One reason for this variation is that squeezing of the hand, such as when shaking hands, may close four devices together along the pin to leave sufficient pin projecting at one end from the assembly as to risk penetration of the tissue. Such a risk is reduced by the use of two assemblies, each of two devices. Also the use of domed end caps will avoid any tendency for the adjacent ends of the pins of such devices to produce a similar result by direct abutment because the caps will slide around each other.

A second reason for this variation is that the hand can more readily adopt a cupped configuration.

Also, a benefit of adopting this variation is that pin threading is facilitated.

Another variation which has arisen during development of the invention is that of the metacarpal component collar from a simple diametral form to one which projects dorsally over the pin-bearing zone. This projection assists in retaining the extensor tendon passing therethrough in a natural location to avoid undue alteration of the joint mechanics in use, and also enhances the cosmetic appearance.

While the present invention has been described with more particular reference to the illustrated embodiment and variations during the development leading thereto, it is not intended to be limited thereby. Indeed the invention is at an early stage of development and is accordingly open to variation within the more general concept thereof first discussed above.

One variation can arise in the choice and distribution of materials in the overall assembly. The present preference centres on the use of metal such as stainless steel and chrome-cobalt alloys, and plastic materials such as ultra high molecular weight polyethylene, which are well established in endoprosthetic devices. In particular, the pin member is of metal to provide strength in the principal stress-distributing integer, while all relative movements involve low friction plastics-metal interfaces. However, other materials are becoming established, yet others are likely to, and the invention is open to the application of other choices when suited to the relevant functions.

A further possibility already mentioned earlier is that of a snap fit mechanism between the bearing portions of each device, this mechanism needing to be only sufficiently strong to stabilise the desired coaxial relationship for the purpose of threading the pin member.

Another possibility is that some allowance may need to be made for variation of the relative dispositions of the pin member and the metacarpal components, the former being of predetermined geometry and the latter forming a substantially fixed array determined in large part by the anatomy of the recipient hand. In particular, variation in the relative angular disposition of the pin member and each individual metacarpal component can be afforded by necking the bored arm portion of the latter at the junction with its collar to allow bending of the bored portion, or by divergent flaring of the bore towards its ends.

The above possibilities for variation can each relate to the presently preferred form of the invention, but this form itself can vary. For example, instead of a common pin member interlinking a plurality of MCP devices, the devices may have transverse projections which interlink one device only to a neighbouring device, in telescopic manner, say.

Lastly, it is to be noted that the variations of sizes which exists between individual MCP joints and hands can be accommodated by the provision of components with a range of stem and/or stem socket sizes, and a range of pin member lengths, while retaining uniformity in the pin-bearing portions and the cross-sectional shape and size of the pin member.

We claim:

1. An endoprosthetic MCP joint assembly (10) comprising a plurality of devices (11) which each include a pair of phalangeal and metacarpal components (12, 13) for respective connection to the bones of an individual MCP joint, and wherein each of said devices include a common pin member (14) hingedly connecting the components of each of said devices.

2. An assembly according to claim 1 wherein each said phalangeal component comprises two sub-components of which one (20) is connectable with a respective bone and the other (15) of which is connected with said pin member, said other sub-component being slidably and rotatably received in said one sub-component.

3. An assembly according to claim 2 wherein each said phalangeal component has a bifurcated portion (17) of which the arms (18) embrace an arm (25) extending from the respective metacarpal component, said arms being coaxially bored with the pin member passing therethrough to hingedly connect the same.

4. An assembly according to claim 3 wherein said phalangeal one sub-component and said metacarpal component are of plastics material, said phalangeal other sub-component and said pin member are of metal, and said bifurcated arms are provided with bushes (19) of plastics material to receive said axle member.

5. An assembly according to any of the preceding claims wherein said pin member has a respective radially enlarged stop (27) at each end thereof, at least one such stop being separably connected to the pin member.

6. An assembly according to claim 5 wherein each said stop is of domed form.

7. An assembly according to claim 5 wherein each said stop is of plastics material connected by a snap fit in cooperation with a respective groove (26) around said pin member.

8. An assembly according to claim 5 wherein each of said phalangeal and metacarpal components of each of said devices comprises an elongate portion (15/20, 22) for connection with a respective bone, and respective hinge portions (17, 25) at one end thereof connected with said pin member, said elongate portions both being transversely off-set in a common direction relative to said pin member with said metacarpal component elongate portion (22) being so off-set to a greater extent.

9. An assembly according to claim 8 wherein said metacarpal component hinge portion (25) is, at its side in said off-set direction, extended axially of said pin member to shroud said phalangeal component hinge portion.

10. An assembly according to claim 5 wherein said pin member is longitudinally curved.

11. An assembly according to claim 10 wherein said pin member is connected with each said device to present a concave curvature facing said metacarpal component thereof.

12. A set of parts adapted for connection to form an assembly according to claim 5.

13. A method for surgical treatment which comprises connecting a pulurality of endoprosthetic hinge devices each including a pair of phalangeal and metacarpal components for respective connection to the bones of an individual MCP joint and mechanically interconnecting each of said devices with a common pin member through a hinge portion of said components to stabilize the same against ulnar drift.

* * * * *